United States Patent [19]
Rosenberg

[11] Patent Number: 4,665,069
[45] Date of Patent: May 12, 1987

[54] ANALGESIC COMPOSITION AND METHOD OF RELIEVING PAIN

[76] Inventor: Barnett Rosenberg, 2410 College Rd., Holt, Mich. 48842

[21] Appl. No.: 719,239

[22] Filed: Apr. 2, 1985

[51] Int. Cl.$^4$ ..................... A61K 31/34; A61K 31/54; A61K 31/505

[52] U.S. Cl. .................................. 514/222; 514/267; 514/471; 514/817; 514/969; 514/970

[58] Field of Search ............... 514/969, 817, 471, 265, 514/221, 970

[56] References Cited

PUBLICATIONS

Chem. Abst., 20696 a (1969).
Holford et al., Current Therapeutics, Jan. 1984, pp. 13-18.
Shaw et al, Brit. Med. Journal, vol. 283 (pp. 875-876), 6-3-81.
JAMA, Peters, vol. 243, p. 565 (2-8-80).
Hadgraft-International Journ. Pharmaceutics, vol. 16, pp. 255-270 (1983).
Cabana, Drug Development & Industrial Pharmacy, vol. 9, pp. 707-724.

*Primary Examiner*—Stanley J. Friedman
*Attorney, Agent, or Firm*—Dennis P. Clarke

[57] ABSTRACT

An analgesia composition comprising an aqueous solution of a neurologically active agent in a concentration of from about $10^{-3}$ to about $10^{-13}$ grams/ml and a method of relieving pain comprising topically applying the composition to the genitalia of a human or non-human animal.

10 Claims, No Drawings

ANALGESIC COMPOSITION AND METHOD OF RELIEVING PAIN

BACKGROUND OF THE INVENTION

FIELD OF THE INVENTION

The invention relates to analgesic compositions and a method for the relief of pain.

PRIOR ART

In 1973, conclusive evidence surfaced of the existence of specific opiate binding sites in the brain [Simon et al, Proc. Natl. Acad, Sci., U.S. A., 70: 1947 (1973); Pert et al, Science, 179: 1011 (1973); Terenius, Acta Pharmcol. Toxicol., 32: 317 (1973)]. This evidence eventually led to the discovery of the endogenous brain opioid peptides [Hughes, Brain Res., 88: 295 (1975); Terenius et al, Acta Pharmacol. Toxicol., 35 (Suppl. 1): 55 (1974)], the endorphins and enkephalins. This and further research led to the conclusion that the brains of all species tested are capable of producing chemicals when suitably stimulated which mitigate the sensations of pain. Effective stimulation may occur by intrinsic, still unknown mechanisms; by electric stimulation of suitable areas of the brain with implanted electrodes [Reynolds, Science, 164: 444 (1969)], by mechanical probing of the vaginal cervix of rats [Crowley et al, Psychopharmacology, 54: 223 (1977)], or by stress [Akil et al, Science, 227: 424 (1985)].

A second and apparently unrelated area of brain research began in 1954, with the discovery by Olds and Milner [J. Comp. Physiol. Psychol., 47: 419 (1954)] of the electrically stimulatable "pleasure centers" in the brain. See *Brain—Stimulation Reward*, (Ed. A. Wauquier and E. T. Rolls), American Elsevier Publishing Co., Inc., New York (1976) for a review of research in this area.

The regions of the brain mapped for pain relief and stimulating the pleasure centers by electrical stimulation are broad and varied. It should not be surprising, therefore, that some degree of overlap occurs. In patients tested for pain with implanted electrodes in various regions of the brain, some have reported pleasant sensations, intense pleasure, and sexual excitement upon electrical stimulation. These anatomic sites include the septal region, mesencephalic tegmentum, the thalamic nuclei, and the frontal and temporal cortex [Delgado, Ibid. 481]. This overlap is not universally true, however, since pleasure center stimulation does not necessarily produce analgesia and vice versa [Mayer et al, Pain, 2: 379 (1976)].

The possibility of some overlap between areas of the brain that stimulate pleasure centers and the production of analgesia led to the formulation of the hypothesis which underlies the present invention, namely, that strong stimulation, by external means, of the sexual apparatus can produce analgesia. It appears to be a biological necessity that sexual stimulation must be pleasurable for a species to propagate; that is, a strong, fairly direct neural link must exist between the genitals and the pleasure centers of the brain, and therefore, possibly the analgesic responses of the brain.

The present invention is predicated on the discovery the certain compositions and methods for the application thereof sufficiently stimulate the sexual apparatus to achieve an analgesic response in the brain. The penis in the male, and the clitoris and vagina in the female, are very rich in mechanoreceptors activated by touch or stretch of the skin and mucous membrane. These receptors make synaptic connections with the ganglia of the pelvic nerve which innervates the genital region. At least some of these neurons are autonomic cholinergic fibers [G. B., Koelle, *The Pharmacological Basis of Therapeutics*, 399 (Ed. by L. S. Goodman and A. Gilman) (The Macmillan Co. New York) Third Edition, 1965]. It is known that cholinergic ganglia are stimulated by nicotine, muscarine, and other related alkaloid drugs [Volle et al, Ibid., p. 578; Douglas et al, J. Physiol. 119: 118 (1953); Gray et al, Brit. Med. Bull., 13: 186 (1975)]. It is further relevant that these organs (glans penis and clitoris) are poorly endowed with pain receptors.

The analgesically effective stimulation must also be produced externally. That is, the stimulating agent must be applied to the skin and mucous membranes of the genitals and must be absorbed in sufficient quantities through the skin to achieve the desired effect.

It is an object of the present invention to provide a composition and method for the relief of pain based on effective strong stimulation of the sexual apparatus.

SUMMARY OF THE INVENTION

One embodiment of the invention is an analgesic composition comprising an aqueous solution of a neurologically active agent adapted for topical application to the genitalia of a human or non-human animal wherein the concentration of the neurologically active agent in the solution is in the range of from about $10^{-3}$ to about $10^{-13}$ grams/ml.

Another embodiment of the invention is a method of analgesia comprising topically administering to the genitalia of a human or non-human animal an analgesically effective amount of an aqueous solution of a neurologically active agent, the solution being adapted for application to the genitalia of a human or non-human animal wherein the concentration of the neurologically active agent in the solution is from about $10^{-3}$ to about $10^{-13}$ grams/ml.

A further embodiment of the invention is a method of analgesia as described above wherein the aqueous solution of neurologically active agent is administered in conjunction with administration to the human or non-human animal of a neurologically nutritive amount of at least one nutrient for the nervous system.

Still another embodiment of the invention includes methods of analgesia as described above wherein the aqueous solution of neurologically active agent is administered to said human or non-human animal in conjunction with parenteral administration thereto of caffeine, diazepam, the smoke of burning tobacco or nicotine containing vapor or spray.

A final embodiment of the invention is an analgesic composition in kit form comprising (1) an aqueous solution of a neurologically active agent adapted for application to the genitalia of a human or non-human animal wherein the concentration of the neurologically active agent is from about $10^{-3}$ to about $10^{-13}$ grams/ml and (2)(a) a neurologically nutritive amount of at least one nutrient for the nervous system; (b) an agent selected from the group consisting of caffeine, diazepam, tobacco adapted for burning and inhalation of the smoke thereof and nicotine containing vapor or spray, or (c) mixtures thereof, the nutrient and/or agent being adapted for parenteral administration to the human or non-human animal.

DETAILED DESCRIPTION OF THE INVENTION

The present invention is predicated on the discovery that the topical application of neurologically active chemicals to the genitals, in concentrations ranging from about $10^{-3}$ to about $10^{-13}$ grams/ml have profound effects on the peripheral and central nervous system. Among these effects are: (1) a relief from pain; (2) a marked increase in the sensitivity of the genital mechanoreceptors; and (3) the induction of nerve signals, originating in the brain, which propagate in a wave throughout the body.

Any neurologically active agent, preferably a cholinergic agonist, ganglionic stimulant or local anesthetic may be employed in the practice of the invention. The most preferred agents are those cholinergic agonists functioning as parasympathomimetic agents. Preferred parasympathomimetic agents are nicotine, muscarine or pharmaceutically acceptable derivatives thereof. Other suitable neurologically active agents include arecoline; pilocarpine; methacholine, oxotremorine and xylocaine.

Nine months of continuous daily testing of the method and compositions produced no evidence of tolerance. Tests for physiologic dependency over an 8 day period were negative.

The range of active concentration of the drugs is enormous, about $10^{-10}$, from the highest concentration tested, to the lowest effective dose. Since there was no unacceptable side effects at the highest dose (1 mg/ml), the method and compositions of the invention have extremely large therapeutic indices. It is a further concluded that the neurologically active agents are primarily affecting the mechanoreceptors, which, like other receptor responses show adaptation and a logarithmic (or power law) dependence of the response to the applied dose.

The method and compositions of the invention were tested on six human subjects of both sexes as described below. All three of the above-described major responses occurred in each subject, thereby establishing that they are not idiosyncratic.

Complete or partial pain relief occurred for the following pains in the various subjects: (1) intense pains (possible arthritis) at the base of the skull; (2) cold sensitivity of teeth; (3) toothache; (4) intense muscular spasm pains in the anus and groin; (5) arthritic pains in the hands and neck; (6) muscle pains in the upper back; (7) knee joint pains; (8) menstrual cramps and post-menstrual muscle pains; (9) headaches; (10) burning pains in legs. In some cases pain remission lasted for months after a few treatments. In most cases, however, continual treatments were necessary. A single treatment provides relief for about 24-72 hours. The evidence and data resulting from the tests suggest that a fairly broad spectrum of pains is susceptible to the treatment of the invention.

All chemicals were tested after dissolving them in Tris-Phosphate solutions buffered at pH 7.5. Stock solutions were serially diluted with the same buffer to a variety of concentrations from $10^{-4}$ grams/ml to $10^{-12}$ grams/ml. Solutions were tested within 48 hours after preparation because of possible lability to light and oxygen of some of the chemicals. The results reported below were obtained at the lower end of the effective concentration range.

Since nicotine and other agents are known to have excitatory effects at low concentrations but produce a blockade of neural responses at higher concentrations, much effort was expended to find a suitable concentration which would produce sufficient excitation without subsequent blockade. This usually can be found in the concentration range of $10^{-9}$-$10^{-12}$ grams/ml but may vary depending on the chemical tested. Surprisingly, it has been found that treatment of the genitals with dilute solutions of L-α-phosphatidylcholine greatly decreases the blockade effect.

Two methods of application were generally used. A cotton swab (holding approximately 0.1 ml of the test solution) was touched to the glans penis or the clitoris for very local tests. For males, a more uniform exposure was achieved by dissolving 0.1 ml of the test solution in 50 ml of warm water in a small plastic cup and immersing the penis in it until some unusual sensations were detected. In women, an opened cotton tampon which has absorbed 25 ml of warm water containing 0.1 ml of the test solution was held against the genitals until sensations were detected (usually 15-30 seconds). Other usable techniques include incorporating the test solution in a water based gel, or a lotion, or cream, bath oils or salts, or bathing in water containing a minute amount of the test solution. In most subjects the treatment was given once a week. In two subjects it was given twice weekly, or more often.

Evidence from the tests utilizing nicotine and phenylephrine suggest that treatment with extremely dilute solutions applied locally to the genitals stimulates a component of the nervous system in the whole body, possibly the parasympathetic system in the case of nicotine, and the sympathetic system in the case of phenylephrine. Apparently, the former produces the more interesting and pleasant response. The latter responses were not pleasant and further tests with phenylephrine were not pursued. The evidence suggests that the subsystem of major interest in these studies of the autonomic nervous system is the parasympathetic, and either nicotine or muscarine, separately produces the desired results.

The subjective responses described by all subjects are very similar. Within minutes of the treatment, neural discharges occur in the brain in a wavelike pattern, coming in 2 or 3 pulses of about 2-3 seconds duration each, and propagating through the upper chest, stomach, lower abdomen, genitals, and finally legs, in that sequence. This may repeat every few minutes for about 15 minutes, and then less often. These waves are, in the main, pleasant or neutral. In one subject they produced a heat sensation in the stomach on passage, which was not pleasant.

Accompanying these uncontrolled neural discharges is a heightened sensitivity to touch in the genitals. Waves can be induced by the merest touch. The main sensations are of a strongly enhanced sexual pleasure which can lead to easy, rapid and strong orgasm. However, other sets of sensations occurred in all subjects which were very different, but, in many cases even more pleasurable than orgasm. These were not directly sexual sensations but were a series of waves of neural discharges from head to toe. These did not cause the tension and tuminescence of sexual sensations, but rather were described as "cool and pleasant". They can be produced continually for many hours. With appropriate timing of their induction, they can be made to pile up to a high intensity ("spikes"). There is evidence to suggest that these waves (spontaneous or induced) are involved in the relief of pain.

The quality of the sensation of the waves varies from neutral to pleasant and appears to be a function of two variables. The first is the adequacy of the treatment and the second is the vitality of the nervous system. Various agents including micronutrients for the nervous system taken orally were tested for their ability to induce or improve the subjective quality of the waves. The following were found in preliminary studies to be of benefit; (1) potassum; (2) manganese; (3) vitamin E; (4) vitamin K; (5) L-α-phosphatidylcholine; (6) choline bitartrate; (7) pantothenic acid; (8) GABA; (9) L-tryptophan; (10) PABA. The following were without any significant effects: (1) calcium; (2) ferrous sulphate; (3) copper (chelate); (4) zinc glyconate; (5) selenium; (6) molybdenum; (7) chromium; (8) biotin; (9) inositol; (10) riboflavin; (11) folic acid; (12) niacin; (13) thiamine; (14) pyridoxine; (15) cobalamin; (16) vitamin A; (17) vitamin C; (18) vitamin D. The following were found to be detrimental; (1) magnesium; (2) iodine. The following nonnutrients were also found to be of benefit: (1) caffeine; (2) diazepam; (3) cigarette smoke or (4) nicotine containing vapor or spray.

Since the treatment appears to stimulate some component of the nervous system throughout the entire body it was not unexpected that some other effects also occurred. These are as follows: (a) bradycardia—in the one subject well studied, the heart rate decreased from a normal value of 72 beats/min. to between 50 beats/min. (morning) to 60 beats/min. (night); (b) increased tone and motility of lower abdomen muscles leading to a normalization of bowel movement; (c) diarrhea after the first treatment but not thereafter, occured in 3 of 6 subjects; (d) lightheadedness and a sense of euphoria; (e) increase in libido (in 2 of 6 subjects); (f) a heat flash accompanying the waves in 1 subject; (g) improved circulation in hands and feet (2 subjects); (h) improved digestion in the one subject well studied with the ability to eat foods which used to cause severe indigestion; (i) elimination of tyramine caused headaches; (j) at the higher dose levels ($>10^{-9}$ grams/ml) an occasional set of muscle twitches in the stomach and legs, short flashes of shooting pains, and a sensation of tightness in the head—all occurring for a short time after treatment; (k) the skin over the entire body has an increased sensitivity to touch and stroking, particularly the lips, thighs and breasts such that stroking of these areas elicits waves.

It can be concluded from the results of the examples set forth below that the heightened activity of the nervous system produces very desirable sensations and pain relief. It is not known whether these results are mediated by the pleasure centers of the brain, or by the innate brain analgesic system, or both. It is clear, however, that a unique, activating link exists between the genital mechanoreceptors and the brain.

EXAMPLE 1

Three human subjects, all young and healthy, were recruited for the following experiments.

The treatment consisted of applying less than 0.1 ml of the test solution, nicotine bitartrate in TrisPhosphate buffer at pH 7.5, at a concentration of $10^{-9}$ grams/ml to the genitals with a brief wipe with a cotton swab. In males it was applied to the glans penis; in females it was applied primarily to the clitoris (beneath the clitoral hood) and occasionally to surrounding labial areas and the vagina.

After ten minutes alone, the subject was asked to report on any unusual sensations. Then, again alone, the subject was asked to probe the genitals for any change in sensitivity to touch. Also, any pains they may have had were listed, and any sensed changes in intensity of pain after the course of treatment (one hour each time) were elicited, as well as reports of any unusual sensations during the week between treatments. This phase of the experiment continued over 22 days.

The following results were reported: (1) all three subjects reported the occurrence of waves of neutral to pleasant sensations, with the same characteristics described above; (2) all three subjects reported a markedly enhanced sensitivity to touch in the genital area, lasting variously from 2 hours to 24 hours, leading in some trials to rapid and intense orgasms; (3) all three subjects reported at some time during the trials the disappearance of pains.

It was noted early during the research leading to the invention that the quality of the responses, the waves, genital sensitivity and completeness of pain relief varied from trial to trial and even day to day. This effect was apart from the known effects of "blockade" by overdoses. On some days the waves were "dull" or neutral, on others "sweet" and intense. It became obvious that the quality of the sensations was, given an adequate treatment, also a function of the status and vitality of the nervous system which could be modified by micronutrients. One of the first micronutrients tested was potassium since it is known to be essential for neural activity. After a treatment the intensity and totality of neural activity, which markedly increased, could deplete the normal nerve cell store of potassium, thus dulling the perceived sensations. This was tested by the volunteer taking ¼ of a 75 mg tablet of KCl during one such dull episode. Within 3–5 minutes the sensations increased, both in intensity and "sweetness". Indeed, a new set of spontaneous waves were generated and lasted for about 15 minutes. Thereafter, for about a day, the sensations were of a better quality. This was repeated a number of times, always with similar results. The presence of potassium in the neurological system is, therefore, deemed essential for good responses.

However, even with potassium being present, there were episodes where the resonses were dull. It appeared likely that other micronutrients were necessary. The following test protocol was established.

EXAMPLE 2

During a time of less than acceptable responses, the volunteer ingested a series of micronutrients with no prejudice in the sequence order. The doses were always ¼ of the recommended daily allowance (where this was known). One was taken every 15–30 minutes. Such rapidity of testing is somewhat unusual, but since any effects or responses occur within that surprisingly short time, it was possible to test a large number of substances quickly in the first screen. The results are given in the tables below as follows: Table I—micronutrients with beneficial effects on the quality of the responses; Table II—micronutrients with little or no beneficial effects on the quality of the responses; Table III—micronutrients with detrimental effects on the quality of responses (usually a shut-off of the phenomena); Table IV—miscellaneous substances with a beneficial effect on the quality of responses.

TABLE I

Micronutrients with Beneficial Effects of the Responses

| Substance | | Optimal Amount |
|---|---|---|
| Potassium Chloride (or gluconate) | 25 mg | 3 times daily |
| Manganese (chelated) | 1.5 mg | 2-3 times daily |
| Choline Bitartrate | 50 mg | 1 time daily |
| L-α-Phosphatidylcholine (Lecithin) | 8 grains | 1 time daily (preferred to Choline Bitartrate) |
| Pantothenic Acid (Calcium Salt) | 5 mg | 1 occasionally (ambiguous at present has also been reported to shut down responses) |
| Para Aminobenzoic Acid (PABA) | 25 mg | 1 occasionally (sometimes causes a lowering of body temperature and chills) |
| Vitamin E | 100 iu | 1 every few days |
| Vitamin K | 25 mcg | 1 every few days |
| Gamma Amino Butyric Acid (GABA) | 25 mg | 1 every few days |
| L-Tryptophan | 100 mg | 1 every few days |

TABLE II

Micronutrients with Little or No Beneficial Effects on the Responses

| Substance | Substance |
|---|---|
| Calcium Carbonate | Vitamin B-2 (Riboflavin) |
| Ferrous Sulphate | Vitamin B-6 (Pyridoxine HCL) |
| Copper Chelate | Vitamin B-12 (Cobalamin) |
| Zinc Gluconate | Vitamin C |
| Selenium (yeast) | Vitamin D |
| Molybdenum Chelate | Folic Acid |
| Chromium (yeast) | Niacin |
| Vitamin A | Biotin |
| Vitamin B-1 (Thiamine HCL) | Inositol |

TABLE III

Micronutrients with Detrimental Effects on the Quality of the Responses

| Substance | Dose Tested |
|---|---|
| Magnesium Gluconate | 7 mg. |
| Iodine | 40 mcg. |

TABLE IV

Miscellaneous Substances with Beneficial Effects on the Quality of the Response

| Substance | Optimal Amount |
|---|---|
| Caffeine | 25 mg, 2 times daily (apart from food sources) |
| Diazepam | ⅛ mg is effective - may take up to 5 mg |
| Cigarette smoke | Each puff on the cigarette (0.8 mg nicotine per cigarette) is a potent wave inducer. A very dilute solution of nicotine in a nasal spray may do the same for non-smokers. |

The results reported herein were retested often. Since active substances can change the baseline responses, they were retested only after the inactives were run through, thus verifying both sets in each test (which were done not less than three days apart). Finally, after the actives were taken, a multivitaminmultimineral, high potency tablet was administered to test if increasing quantities or synergistic effects could produce an increment in the quality of the responses with negative results. The actives are necessary and are sufficient in the amounts listed above. It is surprising that the quantity of a micronutrient that gave maximal responses was always less than the recommended daily allowance. Further, while some of the micronutrients in the active list are not unexpected, others are not known to be required for optimal neural functioning, e.g., manganese. Another unexpected result is the detrimental effects of magnesium and iodine.

All or various sub-combinations of the active micronutrients can be incorporated into one tablet and packaged with the neurologically active agent containing solution in kit form.

EXAMPLE 3

Solutions of other chemicals were prepared in the same manner as described in Example 1, producing test solutions by serial dilution in Tris-Phosphate buffered at pH 7.5 since this is close to the pH of extracellular fluid. This expedient ignores any effects of pH variation on ionization which may change absorption through the skin. All solutions were tested first at a concentration level of $10^{-12}$ grams/ml using the application to the glans of about 0.1 ml of solution by a cotton swab. If not effective, higher doses, by a factor of ten usually, were tried. All solutions were tested within 48 hours to minimize chemical instability problems. The most obvious choices were agents known to have similar effects as nicotine on ganglia, such as arecoline, and pilocarpine. Next were the muscarinic type agents, including muscarine and oxotremorine, which also activate cholinergic ganglia, but possibly at different places (autonomic effector cells) and different surface sites. Methacholine chloride, an analogue of acetylcholine, was also included in this class of parasympathomimetic agents. One adrenergic sympathomimetic agent, phenylephrine, was tested to see if activating the sympathetic system would produce different effects. Finally, one of the class of local anesthetics, xylocaine, was tested. The results are set forth in Table V.

TABLE V

Results of Tests with Neurologically Active Agents

| CLASS | SUBSTANCE | CONCENTRATIONS TESTED | RESULTS |
|---|---|---|---|
| Parasympathomimetics | | | |
| Nicotinic | Nicotine | $10^{-4}$ gms/ml. → $10^{-12}$ gms/ml. | Active over entire range in producing (1) waves (2) genital sensitivity (3) pain relief. Unpleasant side effects at the higher concentration range.* |
| | Nicotine Bitartrate | $10^{-9}$ gms/ml. → $10^{-12}$ gms/ml. | Same as above. |

TABLE V-continued

| CLASS | SUBSTANCE | CONCENTRATIONS TESTED | RESULTS |
|---|---|---|---|
| | Arecoline | $10^{-9}$ gms/ml. → $10^{-12}$ gms/ml. | Same a above. More active waves in cortical region of head. |
| Muscarinic | Pilocarpine | $10^{-9}$ gms/ml. → $10^{-12}$ gms/ml. | Same as Arecoline. |
| | Muscarine | $10^{-10}$ gms/ml. → $10^{-12}$ gms/ml. | As good as nicotine tartrate - Perhaps better in all categories. |
| | Oxotremorine | $10^{-12}$ gms/ml. | Similar to arecoline, but much shorter acting (5 hours compared to days). |
| Acetylcholine analogues | Methacholine | $10^{-10}$ gms/ml. → $10^{-11}$ gms/ml. | Transient (hours) effect on pain relief. Little effect on waves and genital sensitivity. |
| Nicotinic + Muscarinic | Nicotine Bitartrate plus Muscarine (simultaneously applied | $10^{-11}$ gms/ml. | Shut-off all effects for ten days. |
| Sympathomimetic Agents: | | | |
| Adrenergic | Phenylephrine | $10^{-10}$ gms/ml. | No waves, little change in genital sensitivity, no pain relief, pupils dilated. |
| Local Anesthetics | Xylocaine | $2 \times 10^{-12}$ gms/ml. → $10^{-12}$ gms/ml. | Weak activity in all 3 categories. |

*Unpleasant side effects at higher concentrations consist of: nervous discharge in legs, muscle twitches in stomach and abdomen; transient pains in muscles, eyes tearing; transient tightness in head; cloudiness in head.

On the basis of these results it can be concluded that: (1) parasympathomimetic agents are very effective (suggesting that it is the parasympathetic system that is activated); (2) some of these agents are active over an extremely large dynamic range (suggesting that mechanoreceptors are involved as targets); (3) high doses are not dangerous, low doses are effective, and an exact dose is not significant (suggesting non-compliance with standard pharmacology); (4) many agents are absorbed through the skin in sufficient quantities for activity despite a low concentration applied (suggesting that the receptors are close to the surface of the skin or mucous membrane of the genitals); (5) despite extremely local administration of low doses which activate only a small number of receptors, a particular neural sub-system of the entire body is activated (suggesting that some type of "holographic" principle is involved in the central and peripheral nervous system); (6) phenylephrine at a concentration of $10^{-10}$ grams/ml applied locally to the genitals causes almost the same degree and duration of mydriasis as 0.1% solution applied directly to the eye (suggesting, as does other evidence, that there is a unique tight linkage between the mechanoreceptors of the genitals and the brain).

The fact that parasympathomimetic agents, such as nicotine and muscarine, are the best agents in producing the desirable responses does not automatically permit the conclusion that the parasympathetic nervous system is involved. These agents can also act on selected parts of the other nervous systems. If it is assumed, as seems likely, that the receptors of the autonomic nervous system are being activated, then it is necessary to choose between the sympathetic and the parasympathetic systems (or less likely both). Since these two systems operate as opposing forces to produce stability in the organism, the physiologic responses can be examined to determine which system dominates.

Some physiologic effects produced by the treatment have already been specified, bradycardia, increased tone and motility of the gastrointestinal tract, tearing in the eyes, a slight decrease in pupil size, and increased warmth in the extremities (dilation of blood vessels). All of these are characteristic actions of the parasympathetic nervous system. No. physiologic effects that are characteristic actions of the sympathetic nervous system have been observed (with the expected exception of phenylephrine).

On this basis, therefore, it can tentatively be concluded that the treatment of the invention activates the parasympathetic nervous system.

EXAMPLE 4

The three subjects involved in the tests above for generality of the effects each reported some episode of pain relief. Three different subjects, each of whom had intense pains not ameliorated by aspirin were tested for the ability of the treatment to ameliorate such pains. The treatment was the same as Example 1 (0.1 ml of a $10^{-9}$ grams/ml concentration of nicotine bitartrate applied to the genitals one or more times per week). The treatment was very successful in two subjects, producing complete amelioration of pain for a long time (days to months) without the subjects taking any additional pain medication. In the third case, one of advanced arthritis pains of long duration, the treatment helped but was not sufficient to remove all pain. Listed below in Table VI are the varieties of pains remitted by the treatment in all six subjects.

TABLE VI

Types of Pains Remitted in Test Subjects by Treatment

| Type of Pain | Previous Treatment | Results of this Treatment |
|---|---|---|
| Bone pain at base of skull (possibly arthritis) | Aspirin-not effective | Complete remission |
| Toothache (intense) | Aspirin-not effective | Complete remission |
| Cold sensitivity of teeth | — | Complete remission |
| Muscle cramp in shoulder | Aspirin-usually effective | Complete remission |
| Knee joint pain | Chiropractic treatments | Complete remission |
| Menstrual cramps | Aspirin-moderately effective | Complete remission |
| Post menstrual muscle cramps | Aspirin-weakly effective | Complete remission |
| Muscular spasm in anus and groin | Aspirin, Motrin, Flexeril, Darvocet, Darvon - all ineffective | Complete remission |
| Tyramine induced | Aspirin-not effective | Complete remission |

TABLE VI-continued
Types of Pains Remitted in Test Subjects by Treatment

| Type of Pain | Previous Treatment | Results of this Treatment |
|---|---|---|
| headaches Burning sensation in legs | Aspirin-not effective | Complete remission |
| Arthritis pains in joints and neck | Feldene, disalcid- weakly effective | Moderate reduction in pain, increased mobility. |

The two most successful cases were the muscular spasms in the anus and the groin which did not respond even to Darvon. After two treatments, the pain disappeared and the subject was pain free for nearly three months. A third treatment again produced remission.

In the case of the tyramine induced headaches, the subject had previously developed intense, throbbing headaches in the back of the head with the ingestion of even small quantities of chocolate or ripe cheeses. Treatment not only eliminated the headache pains, but the subject now reports that ingestion of chocolate and cheeses produces pleasurable sensations.

It can be concluded, therefore, that the treatment is capable of producing remissions of a wide variety of pains, both minor and major, and in some cases for long durations. Pain remission, in most cases, lasted for 24–72 hours after a treatment The method of application of the neurologically active agents by a cotton swab applied to the very local areas of the genitals is quite effective. Nevertheless, the problem of blockade of the receptors and neurons at higher concentration still produces sporadic shut-off of the responses. Lowering the concentration applied, to below $10^{-9}$ grams/ml is still not sufficient to completely eliminate this problem. With the idea that blockade still occurs because local concentrations in the surface treated may be too high, avoidance of the effect was attempted by using a more diffuse method of application. The application methods described below were successful.

EXAMPLE 5

The first method involved applications to broader areas of the genitals by immersion. The test solution was $10^{-11}$ grams/ml of nicotine bitartrate. 0.1 ml of this was added to 50 ml of warm water in a plastic disposable cup and mixed. The cup was held against the genitals such that the main body of the penis was immersed in the solution. Immersion times of 15 seconds to 15 minutes duration were assayed. The longer times still produced blockade. The condition was then chosen that immersion be continued until some perceptible sign of activity occurred, at which time the cup was removed and the genitals dried. The signs of activity were: (1) muscular contractions in the lower abdomen; (2) head waves; (3) neural discharges in the legs. This technique produced a definite improvement in minimizing the blockade phenomena.

For females an equivalent method involved mixing 0.1 ml of the test solution in 25 ml of warm water. Then a cottom tampon was opened and the full solution absorbed in it. The open tampon was then placed between the open labia so that the clitoral area was covered. The duration was determined as before with similar successful results.

EXAMPLE 6

Techniques to slow the absorption through the skin and mucosal membranes by dissolving the test solution in gels and lotions were also tried with success. Thus, 0.1 ml of the test solution ($10^{-11}$ grams/ml) of nicotine bitartrate was added to 10 ml of K-Y gel in a mortar and well mixed with a pestle. 0.1 ml of the gel was applied to the genitals and left on until signs of activity occurred. It was then wiped off. This worked as well as the immersion technique. It was tried with a variety of water based gels and mineral oil based lotions with equal success. One advantage to this technique is convenience. A second is that preservatives such as methylparaben and propylparaben would increase the stability of the chemicals over time.

EXAMPLE 7

A further test to increase dilution and broaden the surface area for absorption was to add 0.1 ml of the test solution of $10^{-10}$ grams/ml of nicotine bitartrate or arecoline to a bathtub full of water and immerse the body in it. Surprisingly, even such a dilution ($10^{-16}$ grams/ml) produced a significant and pleasant response which lasted for over ten minutes. Thus, another modality for treatment would be a preparation of bath salts or oils containing about 10 picograms or more of the neurologically active chemical per amount required for one bath.

EXAMPLE 8

Despite the effort detailed above to eliminate the blockade effect of nicotine on neural impulses which shuts-off the desirable responses, there remains a residue of sporadic blockade. The following approach minimizes blockade and enhances the desired responses.

While the mechanism of blockade by higher doses of nicotine in neural tissue has not been defined clearly in all cases, there is some evidence in the peripheral nervous system that the ganglionic blockade by nicotine may be due to a competitive type blockade of acetylcholine. If so, then addition of higher concentrations of acetylcholine or analogue or precursor may avoid the blockade.

To test this, purified L-α-phosphatidylcholine was dissolved in chloroform at a concentration of 10 mg/ml and 1 ml of the chloroform solution was added to 9 ml of Tris-Phosphate buffered at pH 7.5. The two phases did not mix, and the chloroform phase became milky. This was sonicated in the cold (in an ice bath) for 15 minutes. The milky suspension did not separate on standing. Then, 1 ml of this suspension was added to 9 ml of buffer. Upon shaking, the vial showed a clear liquid, with a slight light scattering property. The mixture, a colloidal solution at a concentration of $10^{-4}$ grams/ml, was serially diluted as before.

Subsequently, 0.1 ml of the $10^{-11}$ grams/ml of nicotine bitartrate was applied to the glans penis by the immersion method. Shortly afterward, 0.1 ml of the test colloid at a concentration of $10^{-11}$ grams/ml was applied by the same method. There was a weak but definite increase in waves and genital sensitivity. This procedure was repeated with increasing concentrations. At a concentration of $10^{-7}$-$10^{-8}$ grams/ml, there was a very satisfactory response. The waves and the genital sensitivity continued unabated for 24 hours, indicating that the usual blockade was not occurring. This was repeated with many variations, including application with a cotton swab, giving the nicotine before or after the phosphatidylcholine (lecithin) or mixing them together in a test solution for simultaneous topical application (the solution contained $10^{-11}$ grams/ml of nicotine and $10^{-7}$ grams/ml of lecithin), with equally satisfactory results in that blockade did not occur. The results were more stable, repeatable, longer lasting and satisfactory.

EXAMPLE 9

The major problems occur with parenteral administration of endorphins and enkephalins. These are (1) the development of tolerance to the chemical which requires increasing doses to be administered to achieve a given level of analgesia, and (2) the occurrence of dependency, which produces unacceptable effects upon withdrawal from the treatment. It is essential for any new method of analgesia to test for these phenomena.

For the past 9 months the treatment has been tested on volunteers with always decreasing concentrations. For the past 2 months a concentration of $10^{-11}$ grams/ml almost every two days (about 30 treatments) was used. In no test has it every been found necessary to increase the dose to achieve the desired responses. In the test subjects given weekly treatments, no evidence occurred to suggest a diminution of the responses to the standard test doses. It can be concluded from these test results that tolerance does not develop with the treatment.

For a period of 8 days a volunteer took no treatment. He was observed for signs of changes that would signify the development of physiologic dependency upon the treatment. No such signs were observed. There was a decreasing response of the wave generation, the genital sensitivity, and a slight increase of pain of the old type, but no new pains, for the first three days. Heart rate increased from a night time value of 60 beats per minute to 68 beats/min. Surprisingly, on day 4 a return of some waves and some genital sensitivity, a decrease in pain and a return to a heart rate of 60 beats/min. were noted. This remained the same for the duration of the test.

It can be concluded that since there were no discernible withdrawal symptoms over a period of 8 days after treatment cessation, no physiological dependency developed over 6 months of treatment.

EXAMPLE 10

Five months after the treatments began, a volunteer underwent a fairly complete medical checkup to determine if there were any medically significant changes. These tests included an internist workup, a neurological workup, blood and urine chemistry, and a heart stress test. Other than the slowing down of the heart rate, and a slight loss of excess weight, no significant changes or deficits were observed in any of the tests.

It has been further observed that the treatment also reversed a few physiologic deficits that are normally attributed to the aging process. These improvements include: improved sexual function, slowing of the heart rate, improved tonicity and motility of the gastrointestinal tract, improved sense of "feeling good", better digestion, normalization of bowel movement, slightly improved sleep and finally an unprovable but subjectively definite increase in problem solving capacity.

Two subjects under treatment reported a decided improvement in the blood circulation to the extremities. Their hands and feet were much warmer (nearer normal) than usual. One of these subjects had Reynaud's disease. She noted a definite improvement in her conditon.

There is reason to believe that withdrawal symptoms of opiate addicts are due to inadequacy of the brain production of endogenous opiates in the presence, over a long time, of a large exogenous supply. If the method and composition of the invention do indeed stimulate the production of endogenous brain opiates, then they may be of value in treating addicts attempting to overcome their addiction to minimize their withdrawal symptoms.

It will be understood that by the phrase, "in conjunction with", to describe the administration of the micronutrients, blockade inhibitors and enhancing agents (caffeine, diazepam, tobacco smoke or nicotine containing vapor) is meant that topical administration of the neurologically active agent may take place prior to, after or simultaneously therewith.

The micronutrients and other activity enhancing agents may be separately packaged and combined with the neurologically active agent containing composition in kit form for subsequent treatment protocols.

It will be understood by those skilled in the art that by the term, solution, is meant a true solution or dispersion or suspension of the active agent in a form suitable for topical application and absorption by the genitalia.

It will further be understood that in lieu of inhaling tobacco smoke to enhance the effect of the neurologically effective agent, a nasal spray containing nicotine vapor or spray may be administered to the subject.

It will also be understood that, in the case of neurologically active agents which are only difficultly absorbed when topically applied to the skin, they may be dissolved or dispersed in DMSO to enhance absorption.

I claim:

1. An analgesic composition comprising an aqueous solution of a parasympathomimetic agent adapted for topical application to the genitalia of a human or nonhuman animal wherein the concentration of said neurologically active agent in said solution is from about $10^{-3}$ to about $10^{-13}$ grams/ml.

2. An analgesic composition according to claim 1 wherein said parasympathomimetic agent is nicotine or muscarine.

3. An analgesia composition in kit form comprising (1) an aqueous solution of a parasympathomimetic agent adapted for application to the genitalia of a human or non-human animal wherein the concentration of said neurologically active agent is from about $10^{-3}$ to about $10^{-13}$ grams/ml and (2)(a) a neurologically nutritive amount of at least one nutrient for the nervous system; (b) an agent selected from the group consisting of caffeine, diazepam, tobacco adapted for burning and inhalation of the smoke thereof, or a composition adapted for the production of a nicotine containing vapor or spray capable of inhalation, or (c) mixtures thereof, said nutrient and/or agent being adapted for parenteral administration to said human or non-human animal.

4. A composition in kit form according to claim 3 wherein said neurologically active agent is nicotine, arecoline, pilocarpine, muscarine, methacholine, oxotremorine, xylocaine or pharmaceutically acceptable derivatives thereof.

5. A composition in kit form according to claim 3 wherein said nutrient is potassium, manganese, vitamin E, vitamin K, L-α-phosphatidylcholine, choline, pantothenic acid, GABA, L-tryptopham, PABA, or pharmaceutically acceptable derivatives thereof or a mixture thereof.

6. A method of analgesia comprising topically administering to the genitalia of a human or non-human animal an analgesically effective amount of an aqueous solution of a parasympathomimetic agent adapted for applcation to the genitalia of a human or non-human animal wherein the concentration of said neurologically active agent in said solution is from about $10^{-3}$ to about $10^{-13}$ grams/ml.

7. A method of analgesia according to claim 5 wherein said parasympathomimetic agent is nicotine or muscarine.

8. A method of analgesia according to claim 6 wherein said aqueous solution of parasympathomimetic agent is administered in conjunction with administration to the human or non-human animal of a neurologically nutritive amount of at least one nutrient for the nervous system.

9. A method of analgesia according to claim 7 wherein said nutrient is potassium, manganese, vitamin E, vitamin K, L-α-phosphatidylcholine, choline, pantothenic acid, GABA, L-tryptophan, PABA, pharmaceutically acceptable derivatives thereof or a mixture thereof.

10. A method of analgesia according to claim 6 or 8 wherein the aqueous solution of parasympathomimetic agent is administered to said human or non-human animal in conjunction with parenteral administration thereto of caffeine or diazepam or the inhalation of nicotine containing vapor or spray.

* * * * *